US009974973B2

(12) United States Patent
Maxik et al.

(10) Patent No.: US 9,974,973 B2
(45) Date of Patent: *May 22, 2018

(54) SYSTEM AND ASSOCIATED METHODS FOR DYNAMICALLY ADJUSTING CIRCADIAN RHYTHM RESPONSIVE TO CALENDARED FUTURE EVENTS

(71) Applicant: BIOLOGICAL ILLUMINATION, LLC, Cocoa Beach, FL (US)

(72) Inventors: Fredric S. Maxik, Cocoa Beach, FL (US); David E. Bartine, Cocoa, FL (US); Mark Andrew Oostdyk, Cape Canaveral, FL (US); Matthew Regan, Melbourne, FL (US); Robert R. Soler, San Marcos, CA (US); Gregory Flickinger, Indialantic, FL (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/483,327

(22) Filed: Apr. 10, 2017

(65) Prior Publication Data

US 2017/0281967 A1 Oct. 5, 2017

Related U.S. Application Data

(63) Continuation of application No. 14/590,557, filed on Jan. 6, 2015, now Pat. No. 9,827,439, which is a
(Continued)

(51) Int. Cl.
*A61N 5/06* (2006.01)
*A61M 21/02* (2006.01)
(Continued)

(52) U.S. Cl.
CPC .......... *A61N 5/0618* (2013.01); *A61M 21/02* (2013.01); *H05B 33/0863* (2013.01);
(Continued)

(58) Field of Classification Search
CPC .......... A61N 5/0618; A61N 2005/0627; H05B 33/0863; A61M 21/02; A61M 2021/0027;
(Continued)

(56) References Cited

U.S. PATENT DOCUMENTS

| 8,253,336 B2 | 8/2012 | Maxik et al. | |
| 2008/0114219 A1* | 5/2008 | Zhang | A61B 5/02055 600/301 |
| 2011/0084614 A1* | 4/2011 | Eisele | H05B 33/0857 315/152 |

FOREIGN PATENT DOCUMENTS

| JP | 2007-265804 A | 10/2007 |
| JP | 2010-092993 A | 4/2010 |

(Continued)

OTHER PUBLICATIONS

U.S. Appl. No. 14/590,557, filed Jan. 2, 2015.
(Continued)

*Primary Examiner* — Scott T Luan
(74) *Attorney, Agent, or Firm* — Mark Malek; Paul J. Ditmyer; Widerman Malek PL

(57) ABSTRACT

A method is for dynamically adjusting a circadian rhythm of an observer via a user device that includes control circuitry and an associated memory. The method includes accessing a calendar, identifying future events to precondition for and determining a preconditioning schedule for at least one of the identified future events. Determining the schedule includes identifying a circadian shift needed for the at least one identified future event, determining a magnitude of the circadian shift, determining a timeframe for preconditioning, determining a magnitude of a per-day shift based upon the timeframe, and determining if the per-day shift exceeds a maximum allowed per-day shift. Also, the method includes, upon a determination that the per-day shift exceeds the maximum allowed per-day shift, setting the precondi-
(Continued)

tioning schedule responsive to the determination, establishing communication between the control circuitry and a light source, and operating the light source to emit light based upon the preconditioning schedule.

22 Claims, 9 Drawing Sheets

Related U.S. Application Data continuation-in-part of application No. 14/494,290, filed on Sep. 23, 2014, now Pat. No. 9,131,573, which is a continuation of application No. 13/968,914, filed on Aug. 16, 2013, now Pat. No. 8,841,864, which is a continuation-in-part of application No. 13/311,300, filed on Dec. 5, 2011, now Pat. No. 8,686,641, said application No. 14/590,557 is a continuation-in-part of application No. 14/573,922, filed on Dec. 17, 2014, now Pat. No. 9,532,423, which is a continuation of application No. 13/803,825, filed on Mar. 14, 2013, now Pat. No. 8,743,023, which is a continuation-in-part of application No. 13/709,942, filed on Dec. 10, 2012, now Pat. No. 8,760,370, and a continuation-in-part of application No. 13/234,371, filed on Sep. 16, 2011, now Pat. No. 8,465,167, and a continuation-in-part of application No. 13/107,928, filed on May 15, 2011, now Pat. No. 8,547,391, said application No. 13/803,825 is a continuation-in-part of application No. 13/652,207, filed on Oct. 15, 2012, now Pat. No. 8,643,276, which is a continuation of application No. 13/174,339, filed on Jun. 30, 2011, now Pat. No. 8,324,808, which is a continuation-in-part of application No. 12/842,887, filed on Jul. 23, 2010, now Pat. No. 8,253,336, said application No. 14/590,557 is a continuation-in-part of application No. 13/775,936, filed on Feb. 25, 2013, now Pat. No. 9,681,522, and a continuation-in-part of application No. 13/465,781, filed on May 7, 2012.

(60) Provisional application No. 61/643,308, filed on May 6, 2012, provisional application No. 61/643,316, filed on May 6, 2012.

(51) Int. Cl.
| | | |
|---|---|---|
| *H05B 33/08* | (2006.01) | |
| *A61M 21/00* | (2006.01) | |
| *F21Y 115/10* | (2016.01) | |
| *F21S 9/02* | (2006.01) | |
| *F21V 23/04* | (2006.01) | |
| *F21Y 101/00* | (2016.01) | |
| *F21K 9/23* | (2016.01) | |

(52) U.S. Cl.
CPC ............... *A61M 2021/0027* (2013.01); *A61M 2021/0044* (2013.01); *A61M 2021/0066* (2013.01); *A61M 2205/3368* (2013.01); *A61N 2005/0627* (2013.01); *F21K 9/23* (2016.08); *F21S 9/02* (2013.01); *F21V 23/045* (2013.01); *F21Y 2101/00* (2013.01); *F21Y 2115/10* (2016.08)

(58) Field of Classification Search
CPC .. A61M 2021/0044; A61M 2021/0066; A61M 2205/3368; F21S 9/02; F21V 23/045; F21Y 2021/00; F21Y 2115/10; F21Y 2101/00; F21K 9/23
See application file for complete search history.

(56) References Cited

FOREIGN PATENT DOCUMENTS

| JP | 2011-072388 A | 4/2011 |
|---|---|---|
| WO | 2006039789 A1 | 4/2006 |
| WO | 2008146219 A1 | 4/2008 |
| WO | 2009-029575 | 3/2009 |

OTHER PUBLICATIONS

U.S. Appl. No. 14/494,290, filed Sep. 23, 2014.
U.S. Appl. No. 13/968,914, filed Aug. 16, 2013.
U.S. Appl. No. 13/311,300, filed Dec. 5, 2011.
U.S. Appl. No. 14/573,922, filed Dec. 17, 2014.
U.S. Appl. No. 13/803,825, filed Mar. 14, 2013.
U.S. Appl. No. 13/709,942, filed Dec. 10, 2012.
U.S. Appl. No. 13/234,371, filed Sep. 16, 2011.
U.S. Appl. No. 13/107,928, filed May 15, 2011.
U.S. Appl. No. 13/652,207, filed Oct. 15, 2012.
U.S. Appl. No. 13/174,339, filed Jun. 30, 2011.
U.S. Appl. No. 12/842,887, filed Jul. 23, 2010.
U.S. Appl. No. 13/775,936, filed Feb. 25, 2013.
U.S. Appl. No. 13/465,781, filed May 7, 2012.

* cited by examiner

SYSTEM AND ASSOCIATED METHODS FOR DYNAMICALLY ADJUSTING CIRCADIAN RHYTHM RESPONSIVE TO CALENDARED FUTURE EVENTS

RELATED APPLICATIONS

This application is a continuation and claims benefit under 35 U.S.C. §120 of U.S. patent application Ser. No. 14/590,557 titled System For Dynamically Adjusting Circadian Rhythm Responsive To Scheduled Events And Associated Methods filed Jan. 2, 2015 which, in turn, is a continuation-in-part of U.S. patent application Ser. No. 14/494,290 titled Tunable LED Lamp for Producing Biologically-Adjusted Light filed Sep. 23, 2014, now U.S. Pat. No. 9,131,573 issued on Sep. 8, 2015 which, in turn, is a continuation of U.S. patent application Ser. No. 13/968,914 filed Aug. 16, 2013 titled Tunable LED Lamp for Producing Biologically-Adjusted Light, now U.S. Pat. No. 8,841,864 issued Sep. 23, 2014, which is in turn a continuation-in-part of U.S. patent application Ser. No. 13/311,300 filed Dec. 5, 2011 titled Tunable LED Lamp for Producing Biologically-Adjusted Light, now U.S. Pat. No. 8,686,641 issued Apr. 1, 2014.

Furthermore, U.S. patent application Ser. No. 14/590,557 is a continuation-in-part of U.S. patent application Ser. No. 14/573,922 filed Dec. 17, 2014 titled System and Methods for Operating a Lighting Device, now U.S. Pat. No. 9,532,423 issued on Dec. 27, 2016 which, in turn, is a continuation of U.S. patent application Ser. No. 13/803,825 filed Mar. 14, 2013, titled System for Generating Non-Homogenous Biologically-Adjusted Light and Associated Methods, now U.S. Pat. No. 8,743,023 issued Jun. 3, 2014 which, in turn, is a continuation-in-part of U.S. patent application Ser. No. 13/709,942 filed Dec. 10, 2012 titled System for Generating Non-Homogenous Light and Associated Methods, now U.S. Pat. No. 8,760,370 issued Jun. 24, 2014, which, in turn, claims priority from U.S. Provisional Patent Application Ser. No. 61/643,308 titled Tunable Light System and Associated Methods filed May 6, 2012 , U.S. Provisional Patent Application Ser. No. 61/643,316 titled Luminaire Having an Adaptable Light Source and Associated Methods filed May 6, 2012 and is a continuation-in-part of U.S. patent application Ser. No. 13/234,371 filed Sep. 16, 2011 titled Color Conversion Occlusion and Associated Methods, now U.S. Pat. No. 8,465,167 issued Jun. 18, 2013, and is also a continuation-in-part of U.S. patent application Ser. No. 13/107,928 filed May 15, 2011, titled High Efficacy Lighting Signal Converter and Associated Methods now U.S. Pat. No. 8,547,391 issued Oct. 1, 2013, the content of each of which is incorporated by reference herein in their entireties, except to the extent disclosure therein is inconsistent with disclosure herein.

Additionally, U.S. patent application Ser. No. 13/803,825 filed Mar. 14, 2013 is a continuation-in-part of U.S. patent application Ser. No. 13/652,207 filed Oct. 15, 2012; titled LED Lamp for Producing Biologically-Corrected Light, now U.S. Pat. No. 8,643,276 issued Feb. 4, 2014 which, in turn, is a continuation of U.S. patent application Ser. No. 13/174,339 filed Jun. 30, 2011, titled LED Lamp for Producing Biologically-Corrected Light, now U.S. Pat. No. 8,324,808 issued Dec. 4, 2012 which, in turn, is a Continuation-in-port of U.S. patent application Ser. No. 12/842,887 filed Jul. 23, 2010, titled LED Lamp for Producing Biologically-Adjusted Light now U.S. Pat. No. 8,253,336 issued Aug. 28, 2012, the contents of each of which are incorporated by reference in their entireties except to the extent disclosure therein is inconsistent with disclosure herein.

Furthermore, U.S. patent application Ser. No. 14/590,557 is continuation-in-part and claims benefit under 35 U.S.C. §120 of U.S. patent application Ser. No. 13/775,936 filed Feb. 25, 2013 titled Adaptive Light System end Associated Methods and U.S. patent application Ser. No. 13/465,781 filed May 7, 2012 titled Dynamic Wavelength Adapting Device to Affect Physiological Response and Associated Methods, the contents of each of which are incorporated by reference in their entireties except to the extent disclosure therein inconsistent with disclosure herein.

FIELD OF THE INVENTION

The present invention relates to systems and methods for lighting systems for adjusting circadian rhythms.

BACKGROUND OF THE INVENTION

The discordance between an individual's circadian rhythm and the day-night cycle after traveling across time zones, better known as "jet lag," is well known and documented. This discordance is a result in the rapid change of the day-night cycle timing without adequate time for the individual's circadian rhythm to adjust to the new timing. However, it is increasingly evident that the individual's circadian rhythm can be preconditioned prior to travel so as to mitigate the jet lag of the individual. Additionally, evidence increasingly demonstrates that certain types of activity, e.g. physical activity, mental activity, peak at different periods during the circadian cycle. Accordingly, there is a benefit to syncing one's circadian cycle such that these peak periods coincide with a known event that would benefit from such syncing, e.g. aligning the circadian rhythm to peak physical activity performance at the same time as an athletic event, or syncing peak mental performance to coincide with an academic test. However, such systems as are presently available are imprecise and require significant control by the individual to be useful on a frequent basis. Additionally, such systems require the individual to begin preconditioning with sufficient time in advance of the future event so as to adjust the circadian rhythm of the individual without exceeding a maximum circadian shift in a given day. Accordingly, there is a need for a system that is capable of identifying future events requiring or benefitting from the preconditioning of the individual's circadian rhythm and determining a preconditioning schedule accordingly.

SUMMARY OF THE INVENTION

Accordingly, in light of the above, embodiments of the present invention are directed to systems and methods for the dynamic and automated adjustment of an observer's circadian rhythm. An embodiment of the invention provides a method of dynamically adjusting a circadian rhythm of an observer via a user device that includes control circuitry and an associated memory. The method includes accessing a calendar of the observer stored in the memory, identifying one or more future events of the observer to precondition for, defined as identified future events, and determining a preconditioning schedule for at least one of the identified future events. Determining the schedule includes identifying a circadian shift needed, to the circadian rhythm of the observer, for the at least one identified future event, determining a magnitude of the circadian shift, determining a timeframe for preconditioning, determining a magnitude of a per-day shift based upon the timeframe, and determining if the per-day shift exceeds a maximum allowed per-day shift. Also, the method includes, upon a determination that the per-day shift exceeds the maximum allowed per-day shift, setting the preconditioning schedule responsive to the determination, establishing communication between the control circuitry and a light source, and operating the tight source to emit light based upon the preconditioning schedule.

Additionally, or alternatively, in certain embodiments, identifying one or more future events includes determining a time zone within which the future event will occur.

Additionally, or alternatively, in certain embodiments, identifying one or more future events includes accessing future events within a time period from the calendar, and determining which future events need preconditioning.

Additionally, or alternatively, in certain embodiments, the method includes determining if preconditioning schedules for the identified future events conflict, upon a determination that no conflict exists, operating the light source to emit light of the preconditioning schedules, and upon a determination that a conflict exists: querying a user to select one or more non-conflicting future events, receiving an input from the user indicating one or more future events to precondition for, and operating the light source responsive to the input.

Additionally, or alternatively, in certain embodiments, upon a determination that the per-day shift exceeds the maximum allowed per-day shift, further performing: querying the user as to whether to override the maximum allowed per-day shift; receiving an input from the user responsive to the query of whether to exceed the maximum per-day shift; and selecting the preconditioning schedule responsive to the user input.

Additionally, or alternatively, in certain embodiments, the maximum allowed per-day shift is 2.5 hours.

Additionally, or alternatively, in certain embodiments, the method includes monitoring a sleep cycle of the observer, and implementing changes to the preconditioning schedule responsive to the sleep cycle of the observer. As such, monitoring a sleep pattern of the observer may include determining if the observer is asleep, recording signals from a sleep sensor, identifying and recording an indication of low quality sleep from the signals received from the sleep sensor, and determining changes to the preconditioning schedule responsive to the indication of the low quality sleep.

Additionally, or alternatively, in certain embodiments, the sleep sensor an optical motion detector and/or an acceleration detector.

Another embodiment of the invention provides a method of dynamically adjusting circadian rhythm of an observer via a user device that includes control circuitry and an associated memory. The method includes accessing a calendar of the observer stored in the memory, identifying a future event of the observer to precondition for, defined as an identified future event, and determining a preconditioning schedule responsive to the identified future event, by: identifying a circadian shift needed, to the circadian rhythm of the observer, for the identified future event, determining a magnitude of the circadian shift and a related magnitude of a per-day shift needed for the identified future event, and determining if the magnitude of the per-day shift exceeds a maximum allowed per-day shift, and selecting the preconditioning schedule based thereon. The method includes establishing communication between the control circuitry and a light source, and operating the light source to emit light based upon the preconditioning schedule.

Additionally, or alternatively, in certain embodiments, identifying the future event includes determining a time zone within which the future event will occur.

Additionally, or alternatively, in certain embodiments, identifying the future event includes accessing future events within a time period from the calendar, and determining which future events need preconditioning.

Additionally, or alternatively, in certain embodiments, upon a determination that the magnitude of the per-day shift exceeds the maximum allowed per-day shift, further performing: querying the user as to whether to override the maximum allowed per-day shift; receiving an input from the user responsive to the query of whether to exceed the maximum per-day shift; and selecting the preconditioning schedule responsive to the user input.

Another embodiment is directed to a lighting system for dynamically adjusting a circadian rhythm of an observer. The system includes a user device comprising control circuitry and associated memory, and a light source configured for communication with the control circuitry. The control circuitry is configured to access a calendar of the observer stored in the memory, identify one or more future events of the observer to precondition for, defined as identified future events, and determine a preconditioning schedule responsive to the identified future event, by: identifying a circadian shift needed, to the circadian rhythm of the observer, for the identified future event, determining a magnitude of the circadian shift and a related magnitude of a per-day shift needed for the identified future event, and determining if the magnitude of the per-day shift exceeds a maximum allowed per-day shift, and selecting the preconditioning schedule based thereon. The control circuitry is configured to establish communication with the light source, and control the light source to emit light based upon the preconditioning schedule.

Additionally, or alternatively, in certain embodiments, the user device further comprises a communication device configured for communication with the control circuitry and configured to communicate across a network. The communication device is configured to access the calendar and identify future events associated with the observer via the network.

Additionally, or alternatively, in certain embodiments, the control circuitry is further configured to determine a time zone within which the future events will occur.

Additionally, or alternatively, in certain embodiments, the control circuitry is further configured to: access future events within a time period from the calendar; and determine which future events need preconditioning.

Additionally, or alternatively, in certain embodiments, upon a determination that the per-day shift exceeds the maximum allowed per-day shift, the control circuitry is further configured to: query the user as to whether to override the maximum allowed per-day shift; receive an input from the user responsive to the query of whether to exceed the maximum per-day shift; and set the preconditioning schedule responsive to the user input.

Additionally, or alternatively, in certain embodiments, the maximum allowed per-day shift is 2.5 hours.

Additionally, alternatively, in certain embodiments, a sleep sensor is configured to, in combination with control circuitry, monitor a sleep cycle of the observer, wherein the control circuitry is further configured to implement changes to the preconditioning schedule responsive to the sleep cycle of the observer.

Additionally, or alternatively, in certain embodiments, the sleep sensor comprises an optical motion detector and/or an acceleration detector.

BRIEF DESCRIPTION OF THE DRAWINGS

FIG. 4b is a side sectional view taken through line 4b-4b of the system of FIG. 1a.

FIG. 5b is a side sectional view of a lighting device of the lighting system of 5a.

DETAILED DESCRIPTION OF THE INVENTION

Figure 1:
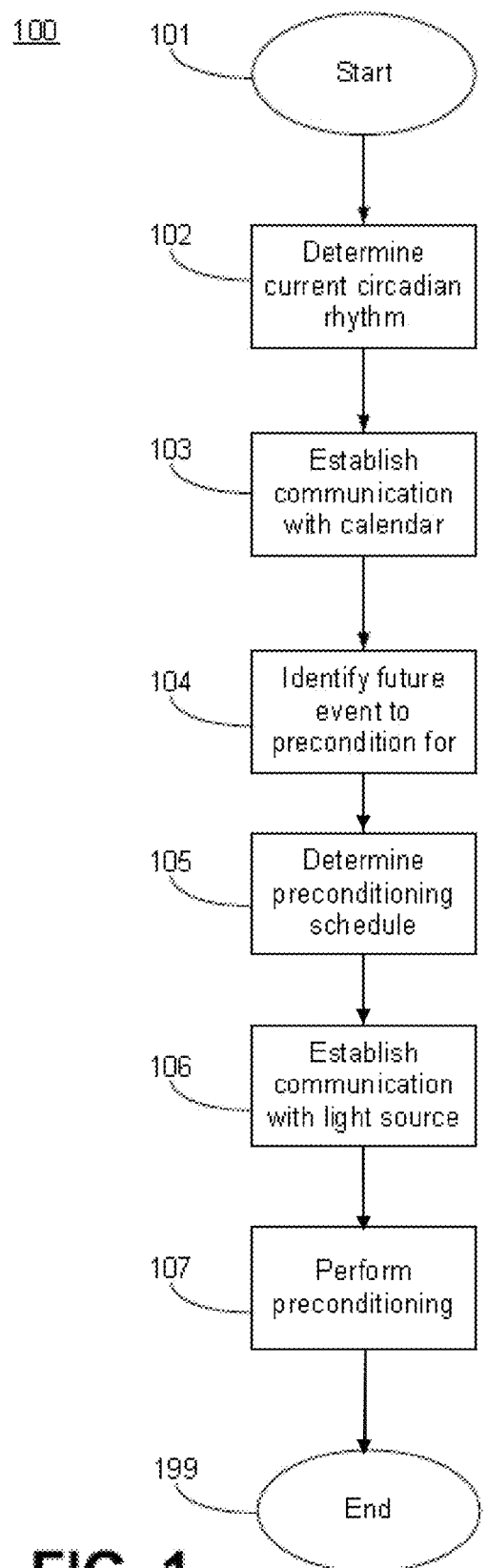
FIG. 1 is a flowchart illustrating a method of operating a lighting device responsive to a calendared event according to an embodiment of the invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

An embodiment of the invention text, as shown and described by the various figures and accompanying text, provides a system for causing illumination that is viewable by an observer to shift a circadian rhythm of the observer responsive to a calendared event for the observer. The means by which the illumination is caused to affect the shift may vary, including adjustment of the spectral power distribution (SPD) of light emitted by a light source associated with a user device, adjustment of the SPD of a lighting device in communication with a user device, or filtering of light emitted by a light source prior to observation by the observer by a filtering device. In each case, the determination of whether and how to cause a circadian shift in the observer may be made based upon the identification of an upcoming event on a calendar associated with the observer, evaluation of the SPD of light currently visible by the observer, and adjustment thereof.

Referring now to FIG. 1, a flowchart illustrating a method 100 of operating a lighting device responsive to a calendared event is presented. Starting at Block 101, the system may determine the current circadian rhythm of an observer of a lighting device at Block 102. The determination of the current circadian rhythm may include at least determining an approximate waking time and an approximate sleeping time of the observer. More specifically, the determination of the current circadian rhythm may include at least determining at what time the observer wakes up and what time the observer goes to sleep. More information regarding the determination of the current circadian rhythm of the observer may be found in U.S. Provisional Patent Application Ser. No. 61/936,654 titled System for Detecting and Analyzing Motion for Pattern Prediction and Associated Methods filed Feb. 6, 2014 and U.S. Provisional Patent Application Ser. No. 61/785,209 titled Method for Controlling Blood Glucose Production filed Mar. 14, 2013, the contents of each of which are incorporated by reference in their entirety, except to the extent disclosures made therein are inconsistent with disclosures made herein. In some embodiments, the system may infer an approximate wake-up time and going to sleep time based on the calendar of the observer, which will be discussed in greater detail hereinbelow. Accordingly, although the step of determining the current circadian rhythm is disclosed first in the method 100, it is not necessarily performed first in time in every embodiment of the invention.

Next, at Block 103, the system may establish communication with the calendar associated with the observer. Establishing communication with the calendar may be accomplished by various means a method, as will be discussed in greater detail hereinbelow. The calendar may include a variety of events.

Upon establishing communication with the calendar, at Block 104 the system may identify a future event on the calendar associated with the observer to precondition for. The term "precondition" may be understood to include the meaning of shifting the circadian rhythm of the observer so as to align the observer's circadian rhythm with the future event. More information regarding affecting a circadian shift may be found in U.S. patent application Ser. No. 13/968,875 titled Tunable LED Lamp for Producing Biologically-Adjusted Light filed Aug. 16, 2013, the content of which is incorporated by reference in its entirety herein, except to the extent disclosure made therein is inconsistent with disclosure made herein, and U.S. Provisional Patent Application Ser. No. 61/785,209, which is incorporated by reference hereinabove.

At Block 105, the system may determine a preconditioning schedule. The preconditioning schedule may be configured to shift the circadian rhythm of the observer incrementally between the present time and time associated with the future event. More specifically, the system may determine a day-by-day schedule of lighting configurations that are configured to shift the circadian rhythm of the observer. More information regarding a daily lighting schedule, and the identification of patterns associated therewith, may be found in U.S. Provisional Patent Application Ser. No. 61/923,924 titled Luminaire for Varying Biologically-Adjusted illumination According to a User-Controllable Circadian Pattern and Associated Systems and Methods filed Jan. 6, 2014, the content of which is incorporated by reference in its entirety herein, except to the extent disclosure made therein is inconsistent with disclosure made herein.

At Block 106, the system may establish communication with a light source. The type of communication the system establishes with the light source may depend on the nature of the system. In some embodiments, the system may be configured to directly control the operation of the light source, in which case the electrical communication with the light source will likely have already been established. Some embodiments, the system may be configured to establish technical communication with the light source across a network, as will be described in greater detail hereinbelow. In such embodiments, the system may so establish electrical communication with the light source, either directly or indirectly through an intermediate computerized device, such as a microcontroller. In some embodiments, the system may be configured to be positioned in optical communication with the light source. In such embodiments, the element of the system may be positioned intermediate the light source and the observer, such that all light emitted by the light source must first pass through the element of the system prior to being observed by the observer.

At Block 107, the system may begin performing preconditioning according to the preconditioning schedule determined at Block 105. Depending upon the requirements of the preconditioning schedule, the system may begin increasing or reducing the intensity of light within certain wavelength ranges so as to affect a biological response in the observer. In some embodiments, this may be accomplished by the system controlling the operation of the light source so as to alter the SPD of light emitted thereby. In some embodiments, this may be accomplished by applying an optical filter to the light source so as to reduce the activity of light within one or more wavelength ranges. More information regarding the various embodiments that the system may take is provided hereinbelow. The system may end at Block 199.

Additionally, in some embodiments, the step of performing the preconditioning may include communication with the observer regarding certain activities he or she may engage in or abstain from so as to enhance the effectiveness of the preconditioning. For example, the preconditioning may include recommended times at which to wake up, go to sleep, eat meals, exercise, and the like. Moreover, the preconditioning may include suggesting the observer consume or avoid certain foods and drinks, such as avoiding caffeine or other substances that may affect sleep quality. In some embodiments, the communication to the observer may take the form of entering new events onto the calendar associated with the observer, sending a message to the observer by any method known in the art, including text message, and the like, to any phone number or e-mail address associated with the observer. Additionally, in some embodiments, an application for a smartphone, as is known in the art, may provide the above-described communications on a smartphone of the observer.

Figure 2:
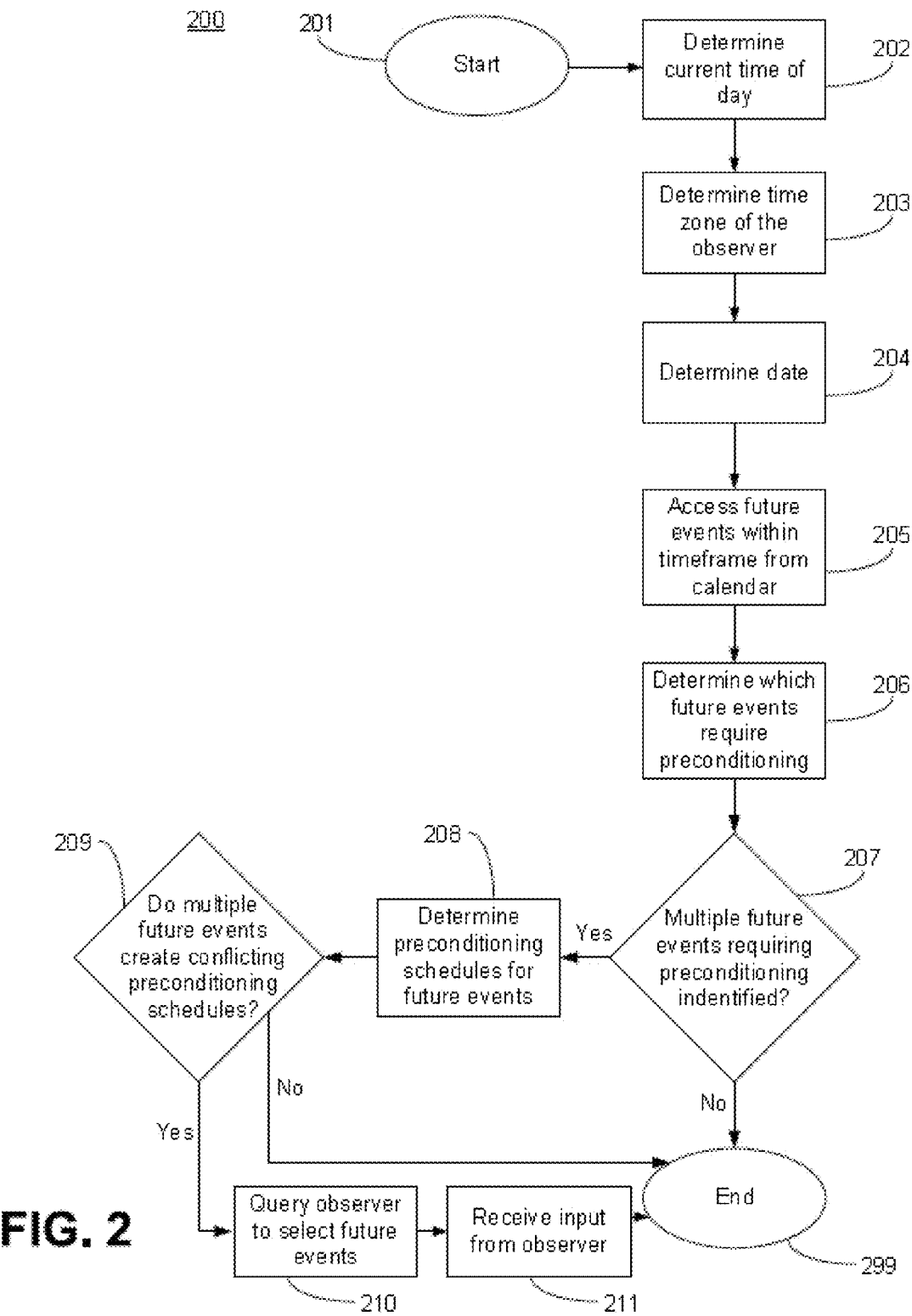
FIG. 2 is a flowchart illustrating a method of identifying a future event requiring preconditioning according to the embodiment depicted in FIG. 1.

Referring now to FIG. 2, additional details regarding the determination of a future event to precondition for are discussed. More specifically, the step of identifying the future event may comprise the steps illustrated in method 200 depicted in FIG. 2. Starting at Block 201, the system may first determine a current time of day at Block 202. In such embodiments, the system may include a dock that is configured to provide a time of day. Additionally, in some embodiments, the system may be configured to receive an indication of the time of day from an outside source across a network, such as the Internet, as is known in the art. Furthermore, in some embodiments, where the system includes a smartphone or other similar device, including a calendar feature, the time of day may be determined by accessing the time of day as maintained by the calendar feature of the smartphone.

Continuing at Block 203, the system may determine a current time zone of the observer. In some embodiments, the system may be configured to determine time zone by receiving an indication from a location lighting device associated with the system. Types of devices include, but are not limited to, a global positioning system (GPS) device. Additionally, in some embodiments, the system may be configured to determine the time from by analyzing an IP address assigned to a network interface device associated with the system, as is known in the art. In each case, the geographical location indicated thereby may be compared to a map delineating the various time zones. In some embodiments, the map may be stored locally on the system. In some embodiments, the map may be accessible by the system via the Internet. Any method of determining the times of associated with the current position of the system is contemplated included within the scope of the invention. Additionally, it is contemplated and included within the scope of the invention that information regarding the time zone of the observer may be determined concurrently with the determination of the time of day, and as such may not constitute a discrete step.

At Block 204, a date associated with the time of day and the time zone associated with the observer may be determined. The date may be determined according to any of the methods described hereinabove related to the determinations of the time of day and the time zone.

At Block 205, the system may access all future events for a given time frame from the calendar. The timeframe for which future events are accessed may be configured by the user, who, in some embodiments, may be the observer. A default configuration may be all future events occurring within the range from about one day in the future to about 12 days in the future. Any timeframe may be selected, and any range from one day to 365 days is contemplated included within the scope of the invention.

At Block 206, the system may analyze the accessed future events to determine which, if any, required or would benefit from preconditioning. The analysis performed by the system may include various considerations. As the nature of the event, the time of day in which the event into occur, and the time zone in which the event is to occur. For example, the system may identify, that an event requiring physical activity may be scheduled to occur at a time that does not coincide with the optimal window of time in the observer's circadian rhythm for physical activity. As another example, the system may identify an event requiring mental performance that may not coincide with the optimal window of time in the observer's circadian rhythm for mental activity. As another example, the system may identify an event scheduled to occur in a time zone that is different than the present time zone of the observer. The scenarios provided herein are exemplary only, and any situation whereby a shift in the circadian rhythm of the observer that may advantageously align the observer's circadian rhythm so as to best correspond to the future event is contemplated included within the scope of the invention.

Additionally, in order for the system to be able to perform the analysis, it is contemplated and included within the scope of the invention that the future events contained in the calendar include information sufficient to be analyzed by the system in order to make the above determinations regarding the nature of the event, the time of day the event is to take place, in the time zone in which event is to occur. As to the nature of the event, a brief description of the event may be included, such as, for example, indicating the observer is to play in a sporting event, indicating the observer is to take an academic test, or any other scenario that may suggest a need for physical and/or mental performance. As to the time of day of the event, an indication of the time may be included. As to the time zone of the event, and address, or at least an identification of the city, state, and/or country within which the event is occur may be included. Moreover, the system may include software capable of interpreting the information included with each event so as to perform the above analysis.

In the event it is determined that no future events require precondition, the system may cease performance of method 200 as well as method 100 of FIG. 1.

At Block 207, the system may determine if more than one future event requiring preconditioning has been identified. If it is determined at Block 207 that there is not more than future event requiring preconditioning, the method 200 may end at Block 299. However, if it is determined at Block 207 that multiple future events require preconditioning, the system may determine a preconditioning schedule for each future event at Block 208. Then, at Block 209, the system may compare the preconditioning schedules of each of the future events to determine if the preconditioning schedules for the future events would create a conflict between their respective preconditioning schedules, whereby the system could not concurrently precondition the observer for both future events. If the preconditioning for the future events does not create a conflict, the method 200 may end at Block 299. However, if the preconditioning for the future events does create a conflict, the system may query the user to select one or more future events to precondition for that does not create a conflict at Block 210. Accordingly the system may either comprise, or be positioned in electrical communication with, a user interface including a user input device. The system may receive an input from the user at Block 211 indicating which of the future events to precondition for. The method may then end at Block 299.

Figure 3:
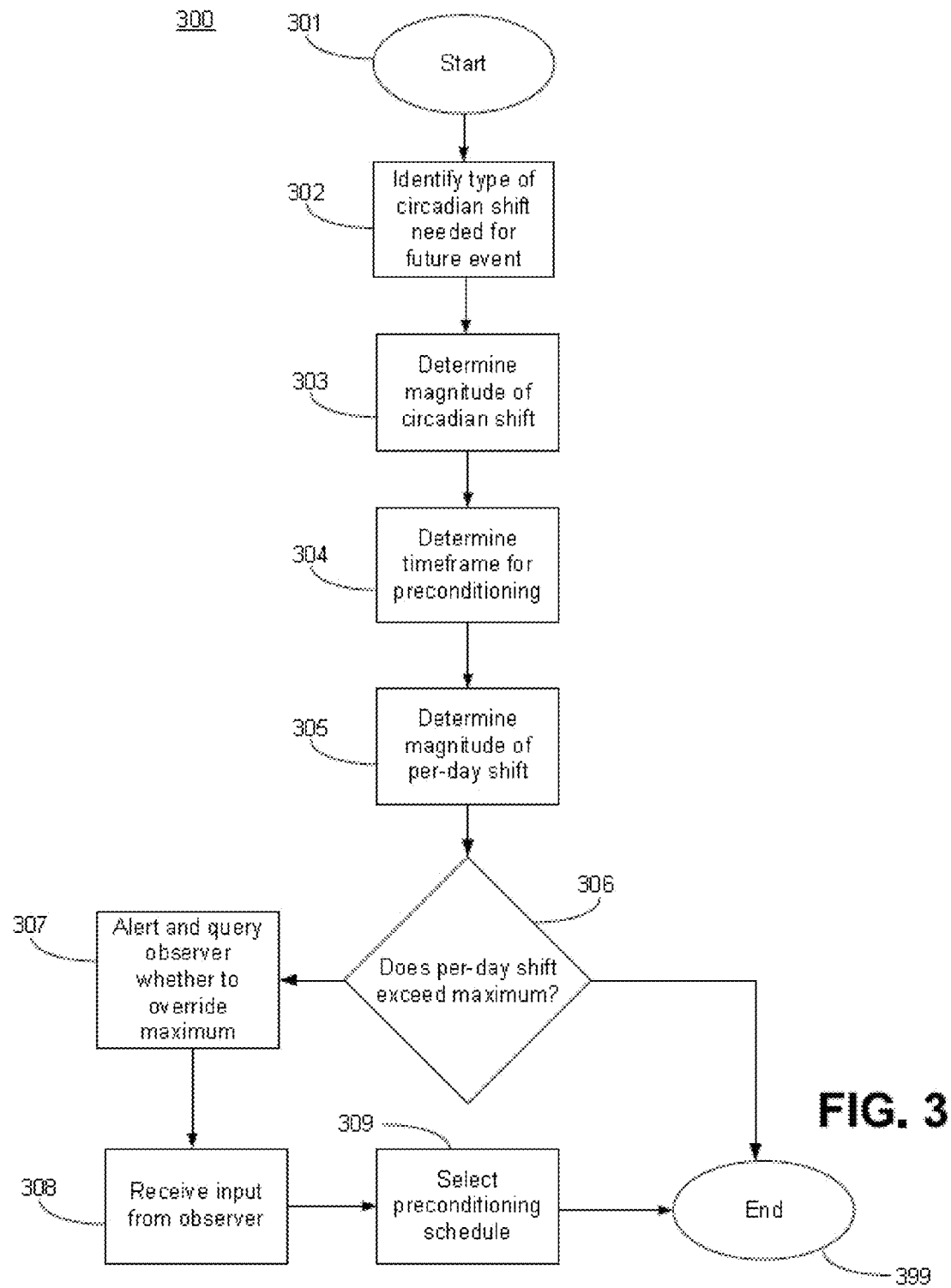
FIG. 3 is a flowchart illustrating a method of determining a preconditioning schedule according to the embodiment depicted in FIG. 1.

Referring now to FIG. 3, additional aspects of the system will now be discussed. Specifically, FIG. 3 illustrates a method 300 related to the determination of the preconditioning schedule will now be discussed. More specifically, the step of determining the preconditioning schedule May comprise the steps illustrated in method 300 depicted in FIG. 3. Beginning at Block 301, the system may analyze the future event to precondition for to identify what type of circadian shift at Block 302, i.e. whether the circadian rhythm of the observer must be advanced or delayed. More information regarding circadian shifts may be found in U.S. Provisional Patent Application Ser. No. 61/785,209, which is incorporated by reference hereinabove.

At Block 303, the system may determine the magnitude of the circadian shift needed to precondition for the future event. The magnitude may be understood to me the difference between the current state of the observer's circadian rhythm and the future state upon performance of the preconditioning.

At Block 304, the system may determine the timeframe within which the preconditioning is to be accomplished. This may be understood to mean the difference between the present time and date and the time and date of the future event.

At Block 305, the system may calculate the magnitude by which the circadian rhythm must be shifted per-day to precondition in time for the event, i.e. how many hours/minutes must the circadian rhythm be advanced/delayed per-day.

At Block 306, the system may determine if the magnitude of the shift per-day exceeds a maximum per-day magnitude. In the present embodiment, the default maximum per-day magnitude is about two and a half (2.5) hours. The maximum per-day magnitude may be adjusted by a user, and any maximum per-day magnitude, greater or less than two hours, is contemplated and included within a scope of the invention. If it is determined at Block 306 that the per-day magnitude does not exceed the maximum, the method 300 may end at Block 399.

If it is determined at Block 306 that the per-day magnitude does exceed the maximum, an alert may be presented to the observer advising of such at Block 307 and the system may query the user whether to create a preconditioning schedule that exceeds the maximum or that adheres to the maximum and will not be designed to fully precondition the observer. The system may receive an input from the observer at Block 308 selecting either a preconditioning schedule either exceeding or adhering to the maximum. At Block 309 the system may then select the preconditioning schedule that either exceeds or adheres to the maximum responsive to the input received from the observer at Block 308. The method 300 may then end at Block 399.

Figure 4A:
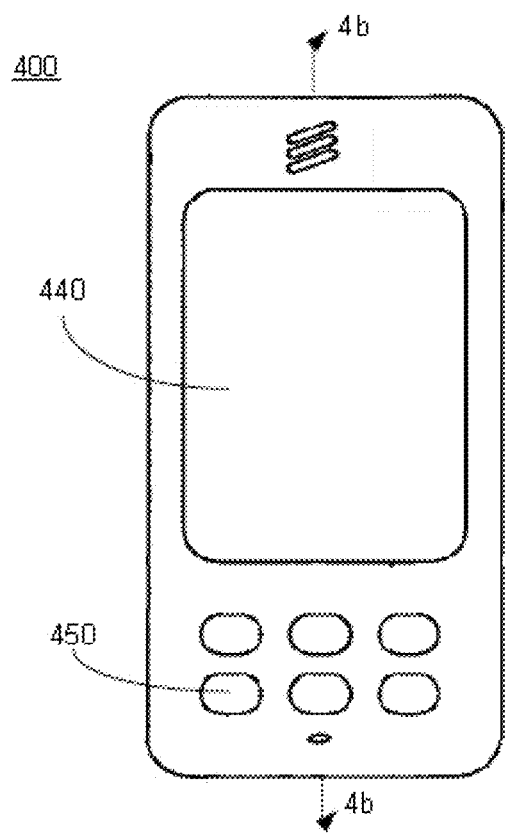
FIG. 4a is an environmental view of a system according to an embodiment of the invention.
Figure 4B:
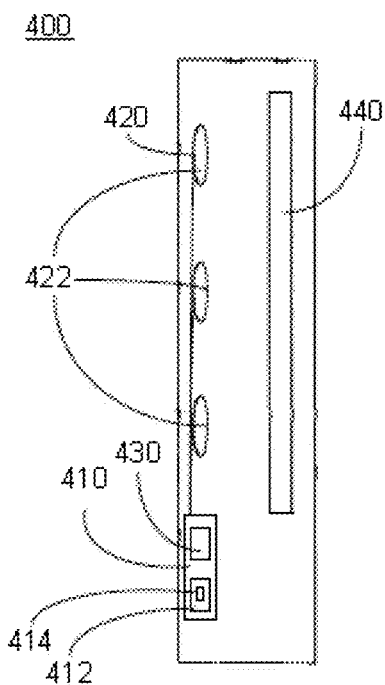

Referring now to FIGS. 4a-b, a system according to an embodiment of the invention is presented. The embodiment may include a user device 400. The user device 400 may be any device capable of emitting light that is observable by an observer. Moreover, the user device 400 may be any device that is capable of adjusting the SPD of light emitted thereby so as to affect a biological response in the observer. More information regarding affecting a biological response in an observer may be found in U.S. patent application Ser. No. 13/968,875 and U.S. Provisional Patent Application Ser. No. 61/923,924, both of which are incorporated by reference hereinabove. Additionally, in the present embodiment, the user device 400 may be any device that is capable of accessing a calendar associated with the observer, identifying an event to adjust light emitted thereby response to, and determining a preconditioning schedule to emit light to affect a shift in the circadian rhythm of the observer. Accordingly, as in the present embodiment, the user device 400 may include control circuitry 410. The control circuitry 410 may have associated therewith a memory 412. In some embodiments, the memory 412 may have stored thereon a calendar 414 associated with an observer.

With reference to the methods of operation illustrated in FIGS. 1-3, the control circuitry 410 may be configured to perform the operations illustrated therein and disclosed in the accompanying description. The various analyses, determinations, and identifications performed by the system described hereinabove may be performed by the control circuitry 410. Additionally, the control circuitry 410 may establish communication with a light source 420 electrically and control operation thereof, as will be described in greater detail hereinbelow.

Additionally, the user device 400 may include a light source 420. The light source 420 may be any type of lighting device as is known in the art, including, but not limited to, light-emitting semiconductors, such as light-emitting diodes (LEDs), incandescent lighting devices, halogen lighting devices, florescent lighting devices, and the like. In the present embodiment, the light source 420 may comprise a plurality of LEDs. In the present embodiments, the light source 420 comprises a plurality of LED banks 422, each LED bank 422 comprising a plurality of LED dies. More information regarding the LEDs and light emitted thereby may be found in U.S. patent application Ser. No. 13/311,300 titled Tunable LED Lamp for Producing Biologically-Adjusted Light filed Dec. 5, 2011, the content of which is incorporated by reference herein except to the extent disclosure therein is inconsistent with disclosure herein.

Additionally, the light source 420 may be operable to emit light so as to affect a biological change in an observer. Specifically, the light source 420 may be operable to affect a circadian shift in an observer, as described hereinabove. Furthermore, the light source 420 may be operable to emit light so as to avoid affecting a biological change in an observer. For example, the light source 420 may be operable so as to suppress the secretion of a hormone, such as, for example, melatonin. Melatonin is an exemplary hormone only, and any hormone that may have its secretion suppressed by the observation light by an observer is contemplated and included within the scope of the invention. More information regarding the suppression of the secretion of hormones may be found in U.S. patent application Ser. No. 13/311,300 and U.S. Provisional Patent Application Ser. No. 61/785,209, both of which are incorporated by reference hereinabove. Furthermore, any other physiological effect that may result in the shifting of the circadian rhythm and may be affected by the observation of light by an observer is contemplated and included within the scope of the invention.

Accordingly, because the control circuitry 410 is positioned in electrical communication with and is configured to control the operation of the light source 420, the control circuitry may be configured to operate the light source 420 according to a preconditioning schedule. More specifically, the control circuitry 410 may be configured to control the SPD of light emitted by the light source 420 so as to shift a circadian rhythm of the observer so as to align the observer's circadian rhythm with a future event.

Additionally, in some embodiments, the user device 400 may include a network communication device 430. The network communication device 430 may be configured to position the user device 400 in communication with a network. Types of networks include, but are not limited to, wireless communication networks, including cellular data networks, Wi-Fi networks, Bluetooth communication, Zigbee communication, and the Internet. The control circuitry 410 may be positioned in communication with a remotely stored calendar associated with the observer via the network communication device 430. In some embodiments, the control circuitry 410 may be configured to store locally a copy of the remotely stored calendar that is accessible via the network communication device 430, the locally stored calendar being the calendar 414 stored on the memory 412. Moreover, the control circuitry 410 may be configured to update the calendar 414 by accessing the remotely stored calendar, identifying differences between the remotely stored calendar and the calendar 414 stored on the memory 412, and updating the calendar 414 responsive to the identified differences.

The present embodiment, the user device 400 may be a computerized device having a display 440. The display 440 may be any device capable of displaying visual content as is known in the art. Types of displays include, but are not limited to, liquid-crystal displays (LCD), cathode ray tube displays (CRT), digital light processing displays (DLP), plasma displays, and the like. The types of displays listed herein are exemplary only, and all displays other known in the art are contemplated included within the scope of the invention. In the present embodiment, the display 440 may be an LCD that is backlit by the light source 420. More specifically, the light source 420 may emit light that passes through the display 440, the SPD of light emitted by the light source 420 being altered thereby prior to observation by the observer.

In some embodiments, the display 440 may be a touch display, capable of receiving inputs from the user via the user touching the screen, either with a finger or a stylus. In such embodiments, user inputs described in FIGS. 1-3 may be received via the display 440. In some embodiments, the user device 400 may include a keypad 450. They keypad 450 may be configured to receive input from the user by the user pressing a key of the keypad 450. These means and methods of user input are exemplary only, and any means or method of receiving an input from the user are contemplated and included within the scope of the invention.

Figure 5A:
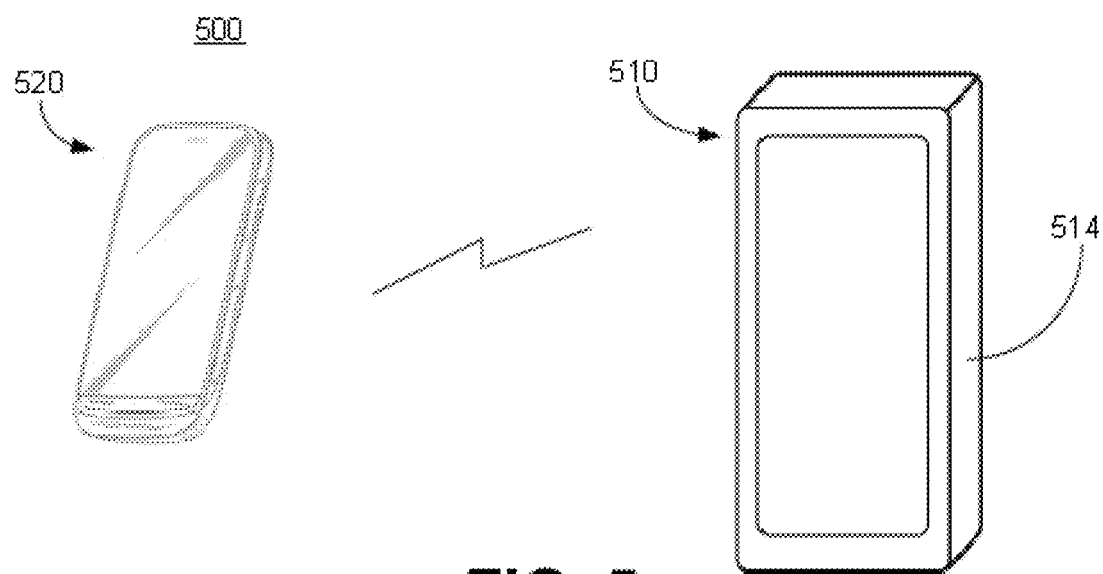
FIG. 5a is an environmental view of a lighting system according to an embodiment of the invention.
Figure 5B:
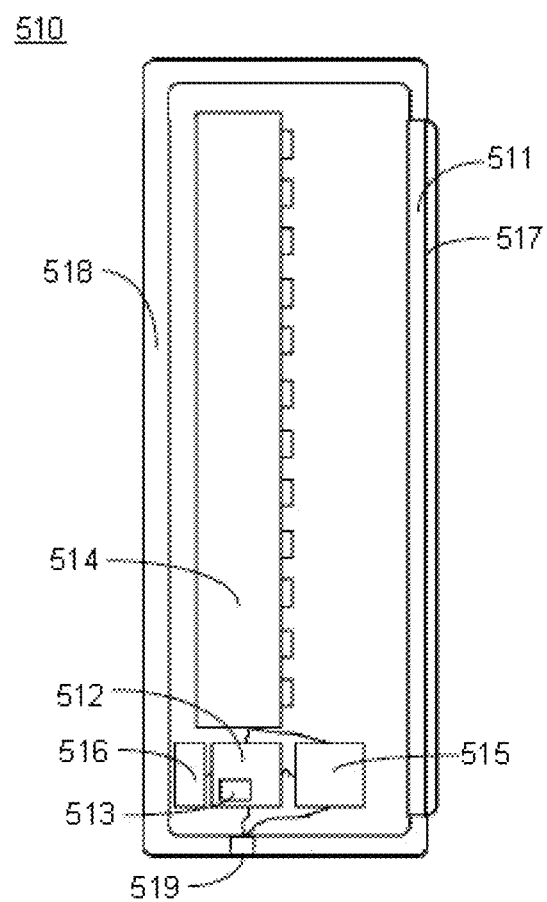

FIGS. 5a-b, an embodiment of the invention is presented. In the present embodiment, a lighting system 500 is provided. The lighting system 500 may include a lighting device 510. The lighting device 510 may be configured to emit light in varying configurations as described in references incorporated hereinabove. Accordingly, the lighting device 510 may include control circuitry 512, a light source 514, and a communication device 516. The control circuitry 512 may be positioned in electrical communication with the light source 514 so as to control the operation thereof to emit light having a varying SPD. Additionally, the control circuitry 512 may be positioned in electrical communication with the communication device 516 and be configured to receive signals thereby and to operate the light source 514 responsive to signals received therefrom. Furthermore, the control circuitry 512 may include a memory 513 as described hereinabove. The lighting device 510 may further comprises a housing 518 configured to generally enclose each of the control circuitry 512, the light source 514, and the communication device 516. The housing 518 may include an electric port 519 configured to be positioned in electrical communication with an external supply of electrical power. The control circuitry 512 may be positioned in electrical communication with the electric port 519 and may further be configured to condition electrical power received from the electric port 519 for use by the various electrical components of the lighting device 510, including the light source 514 and communication device 516.

Additionally, in some embodiments, the lighting device 510 may include a power storage device 515. The power storage device 515 may be positioned in electrical communication with at least each of the control circuitry 512, the light source 514, and the electric port 519, and in some embodiments the communication device 516. The power storage device 515 may be configured to store electric power therein when the electric port 519 is receiving electrical power from an external power source. Additionally, the power storage device 515 may be configured to provide electrical power to elements of the lighting device 510 electrically connected thereto when the electric port 519 is not presently receiving electrical power from an external power source. The power storage device 515 may be any device known in the art capable of storing electrical power, including, but not limited to, batteries and capacitors, including super capacitors and ultra capacitors.

The lighting device 510 may be configured to emit light that is viewable by an observer. More specifically, the light source 514 may be configured to emit light so as to be emitted by the lighting device 510 into the environment surrounding the lighting device 510 so as to be viewable by an observer. In some embodiments, the lighting device may have an emitting aperture 511 through which light emitted by the light source may propagate and be emitted into the environment surrounding the lighting device 510. In some embodiments, the emitting aperture 511 may have positioned therein an optic 517. The optic 517 may be carried by the housing 518. Furthermore, the optic 517 may be transparent or translucent. The optic 517 may be configured to affect the direction light propagating therethrough is emitted therefrom through at least one of reflection or refraction.

The lighting system 500 may further include a user device 520. The user device 520 may be an electrical device configured to electronically communicate with the lighting device 510 so as to provide instructions thereto regarding operation thereof. Accordingly, the user device 520 may be configured to communicate with the communication device 516 of the lighting device 510 by any means or method known in the art, including those methods and standards of communication described hereinabove.

Additionally, the user device 520 may be configured to provide information to a user, who may be the observer, visually, as well as receive inputs therefrom related to the operation of the lighting device 510. The user device 520 may further be configured to receive inputs from the user, and to transmit those inputs to the lighting device 510. The user device 520 may include any type of user input known art, including, but not limited to, keypads, keyboards, a mouse, touchscreen displays, and voice recognition. Any other method of receiving an input from the user is contemplated and included within the scope of the invention.

While the form of the lighting device of the present embodiment is that of a standalone lighting fixture, is it contemplated and included within the scope of the invention that the lighting device 510 may take the form of any lighting device, including, but not limited to, lamps, bulbs, luminaires, and the like. Therefore, any light-emitting device that may perform the above-described functions is contemplated and included within the scope of the invention.

Figure 6:
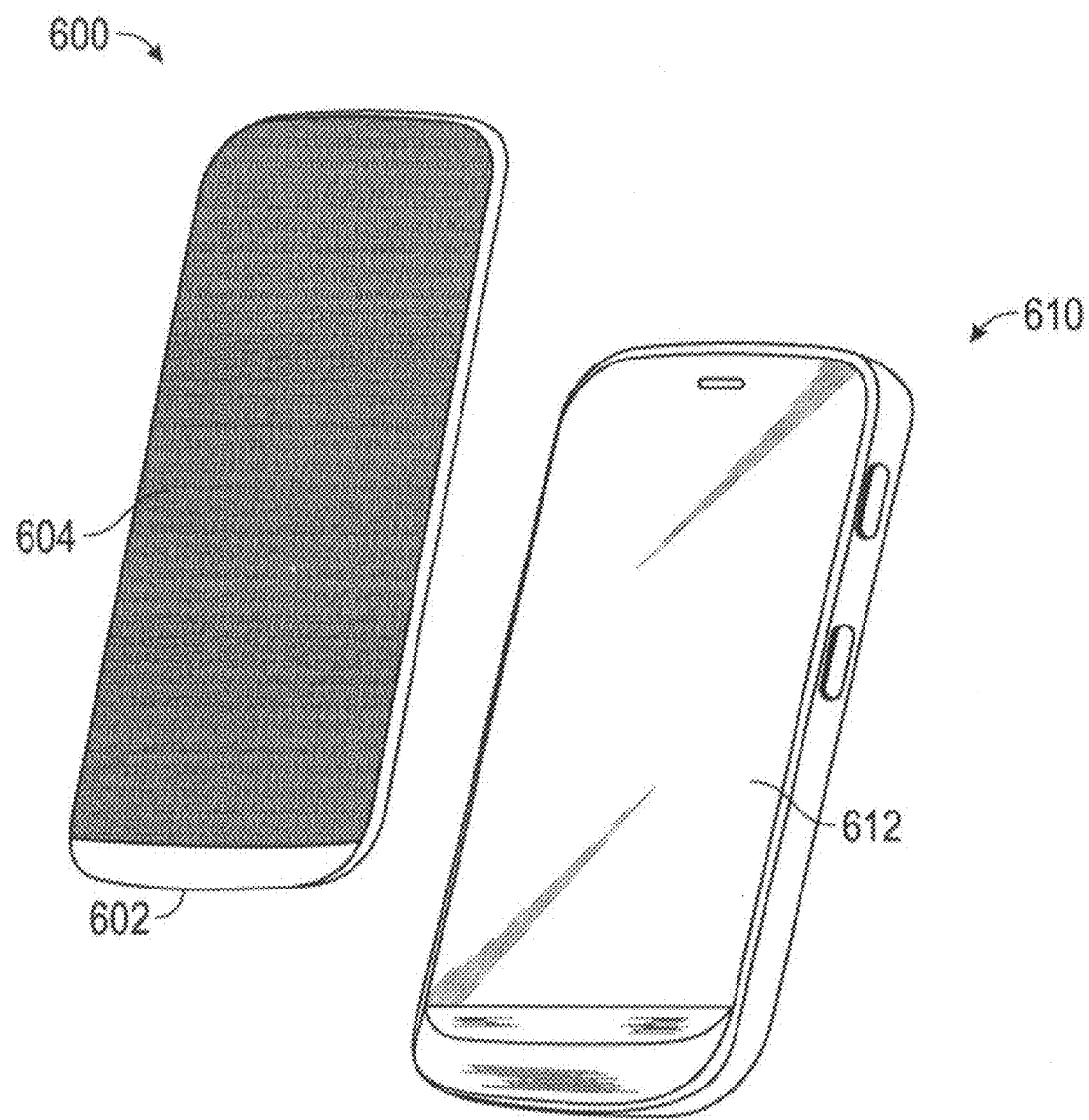
FIG. 6 is an environmental view of a system according to an embodiment of the invention.

Referring now to FIG. 6, an embodiment of the invention is depicted. In the present embodiment, a filtering system 600 is provided. The filtering system 600 may be configured to selectively filter light passing therethrough to. More specifically, the filtering system 600 may be configured to filter light to reduce or eliminate light within one or more wavelength ranges so as to affect or prevent a biological response in an observer. Furthermore, the filtering system 600 may be configured to filter light so as to affect a shift in the circadian rhythm of an observer. In some embodiments, the filtering system 600 may be configured to be attached to a display, such as the display 440 of FIGS. 4a-b. Accordingly, the filtering system 600 presents an alternative to controlling the operation the light source 420 of the user device 400 so as to affect a shift to the circadian rhythm of the observer.

In the present embodiment, the filtering system 600 comprises a frame 602. The frame 602 may be configured to be positioned adjacent or attached to a device configured to emit light. In the present embodiment, the frame 602 is configured to attach to a user device 610 having a display 612. The user device 610 and its constituent elements are not part of the embodiment of the invention. Instead, only the filtering system 600 is part of the present embodiment. The filtering system 600 may further comprise a filter 604. The filter 604 may be carried by the frame 602. Moreover, the frame 600 may be configured so as to position the filter 604 adjacent to the display 612 such that light emitted from the display must pass through the filter 604 prior to being observable by an observer. Accordingly, the filter 604 may be configured to as to permit all light emitted by the display 612 to pass therethrough into the environment. Moreover, the filter 604 may be configured to reduce the intensity of or substantially eliminate light within a wavelength range. The wavelength range associated with the filter 604 may be any wavelength range that is associated with a biological effect in an observer. In the present embodiment, the filter 604 may be configured to substantially reduce or eliminate the intensity of lighting within a wavelength range from about 420 nm to about 490 nm. All other ranges of wavelengths are contemplated and included within the scope of the invention.

In the present embodiment, the user device 610 is a mobile phone, specifically, a smart phone. Any type of device that generates light is contemplated and included within the scope of the invention, including other computerized devices, such as personal computers, as well as devices intended for providing illumination, such as light bulbs, lamps, lanterns, light fixtures, and the like.

The filter 604 may be any filtering device or material as is known in the art. In some embodiments, the filter 604 may be configured to persistently and continuously filter all light passing therethrough, such as a notch filter. In some embodiments, the filter 604 may be configured to be operable to, in a first setting, filter light passing therethrough, and in a second setting, to allow light to pass therethrough unfiltered, hereinafter referred to as an active filter. Such filters are known in the art, utilizing metamaterials known to be selectively operable to filter electromagnetic radiation in the visible spectrum frequency range. In such embodiments, the filtering system 600 may further comprise control circuitry positioned in electrical communication with the filter 604, as well as a power storage device, each as described hereinabove, except to the extent that to control circuitry is configured to control the transition of the filter 604 between the first and second settings, as described. More specifically, the control circuitry may be configured to adjust the filter 604 responsive to a preconditioning schedule so as to affect a circadian shift in an observer as described hereinabove.

Figure 7:
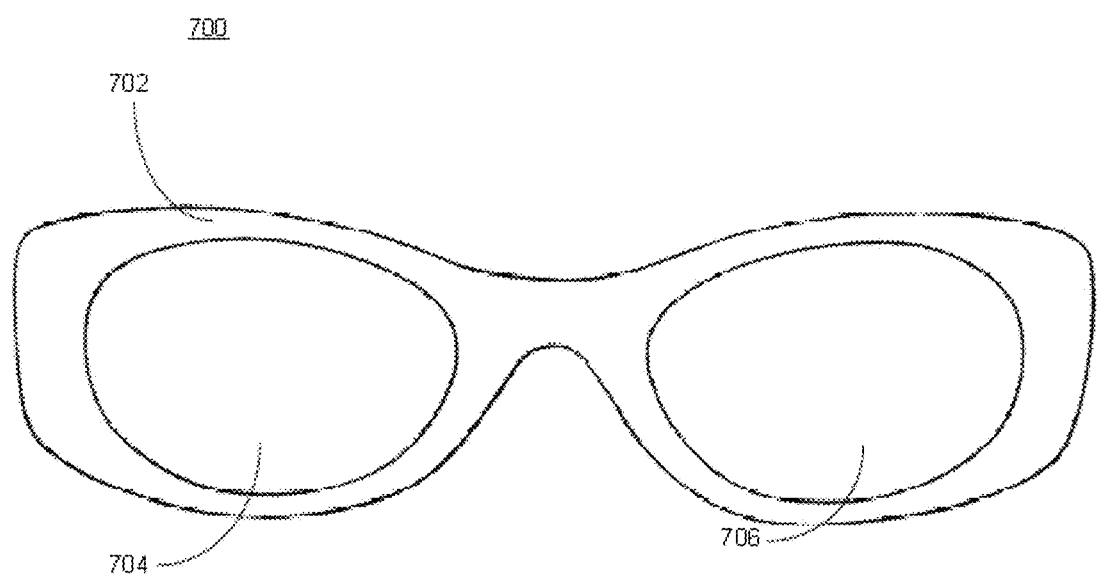
FIG. 7 is an environmental view of a system according to an embodiment of the invention.

Referring now to FIG. 7, an embodiment of the invention is presented. As in the embodiment depicted in FIG. 6, the embodiment comprises a filtering system 700 configured to substantially reduce or eliminate light within a wavelength range from light passing therethrough. However, the filtering system 700 comprises a frame 702 configured to be carried by the ears and nose of an observer, such that the filtering system functions as sun glasses, as is known in the art. Accordingly, the filtering system may be configured to filter light passing therethrough, either from one or more artificial light sources, such as luminaires or light fixtures, or from a natural light source, such as the sun, and from combinations thereof. Moreover, the filtering system may comprise a first filter 704 and a second filter 706, one for each eye of an observer. The first and second filters 704, 706 may include any of the features described for the filter 604 as described hereinabove.

Figure 8:
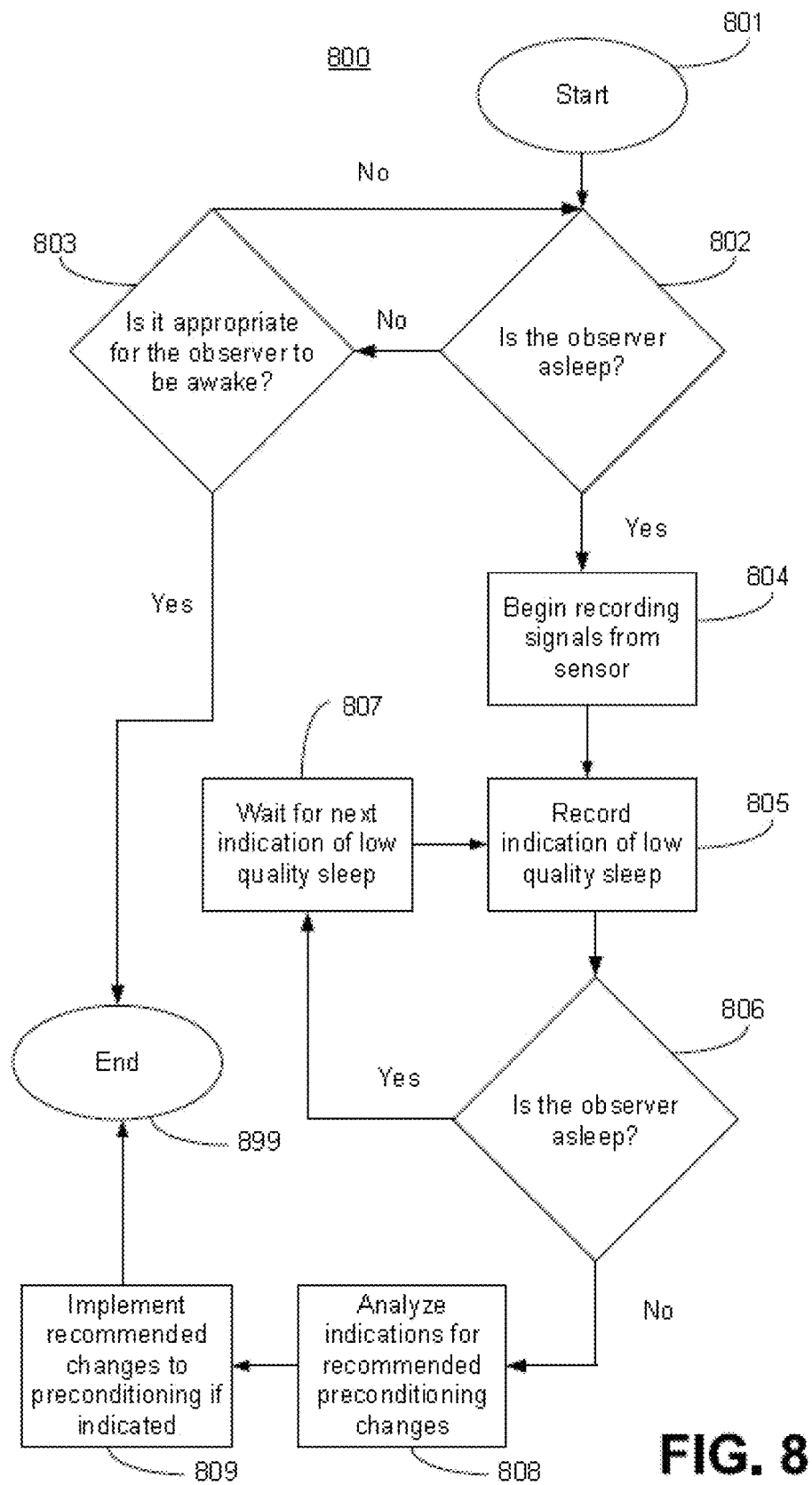
FIG. 8 is a flowchart illustrating a method of monitoring and evaluating the quality of sleep and adjusting a preconditioning schedule responsive thereto according to an embodiment of the invention.

Referring now to FIG. 8, a method according to an embodiment of the invention is presented. FIG. 8 discloses a flow chart illustrating a method 800 of monitoring the quality of sleep of an observer, and altering a preconditioning schedule responsive thereto. The system may include a controller and a sensor for monitoring an indication of the quality of sleep. In some embodiments, the system may be the same system configured to perform the steps illustrated in FIGS. 1-3. In some embodiments, the system may be discrete from the system described in FIGS. 1-3 and may further comprise a communication device configured to communicate with the system described in FIGS. 1-3, either directly or across a network.

Starting at Block 801, the system may determine if the observer is asleep at Block 802. Such a determination may be inferred based on the type of indication received from the sensor. The sensor may be any type of device that may generate a signal receivable by the system from which the quality of sleep of the observer may be inferred. Types of sensors include, but are not limited to, motion detectors, including optically-based detectors, such as LEDs and reverse-biased LEDs, and wearable systems, such as accelerometer-based systems, occupancy sensors, and the like. In some systems, such as accelerometer-based sensor systems, the sensor may be worn by the observer. Moreover, the sensor may be positioned in electrical communication with the controller by any means or method known in the art, including wired and wireless communication, as described hereinabove. More information regarding the monitoring of an observer may be found in U.S. patent application Ser. No. 13/564,345 titled Occupancy Sensor and Associated Methods filed May 4, 2012, U.S. patent application Ser. No. 13/269,222 titled Wavelength Sensing Light Emitting Semiconductor and Associated Methods filed Oct. 7, 2011 and U.S. patent application Ser. No. 13/739,665 titled Motion Detection System and Associated Methods filed Jan. 11, 2013, the contents of which are incorporated by reference herein in their entirety, except to the extent disclosure therein is inconsistent with disclosure herein, and U.S. Provisional Patent Application Ser. No. 61/936,654 which is incorporated by reference hereinabove.

If the observer is determined not to be asleep at Block 802, then at Block 803 the system may determine if the time of day indicates it is appropriate for the observer to be awake at Block 803. Such a determination may be based on a default sleeping time, i.e. about 10 PM to about 6 PM, or it may be based on a learned schedule of the observer, as discussed hereinabove. If it is determined that it is appropriate for the observer to be awake, the method 800 may end at Block 899. If it is determined it is not appropriate for the observer to be awake, the method 800 may return to Block 802. In some embodiments, the system may provide an alert to the observer indicating that it is time to sleep according to any method of alert described herein.

If, at Block 802, it is determined the observer is asleep, the system may begin recording signals from the sensor at Block 804. The signals from the sensor may indicate the quality of sleep of the observer. In that case of motion sensors, an indication of motion may be understood to mean lower quality sleep. Each indication of low quality sleep may be recorded by the system.

At Block 805, a signal indicating low quality sleep is received by the system. At Block 806, the system may determine whether the observer is still asleep, similar to the determination made at Block 802. If it is determined the observer is still asleep, then the system may record the signal indicating low quality sleep at Block 806. Upon recoding the signal, the method 800 may proceed to Block 807, wherein the system waits for the next signal indicating low quality sleep. Upon such a signal, the method 800 may return to Block 805.

If, at Block 806 it is determined the observer is no longer asleep, the system may analyze the recorded indications of low quality asleep to determine if a change to the preconditioning schedule is recommended at Block 808. The determination may be made based upon a number of indications received from the sensor. If the number of indications is equal to or exceeds a threshold number, then the system may recommend changing the preconditioning schedule. Such a change may take the form of reducing the shift scheduled to occur in the day following the previous sleeping cycle. Any other types of changes, including increasing the shift, as well as suggesting various activities to the observer to promote higher quality sleep, is contemplated and included within the scope of the invention. A Block 809, any recommended changes to the preconditioning schedule, if indicated, may be implemented, and the method 800 may end at Block 899.

Figure 9:
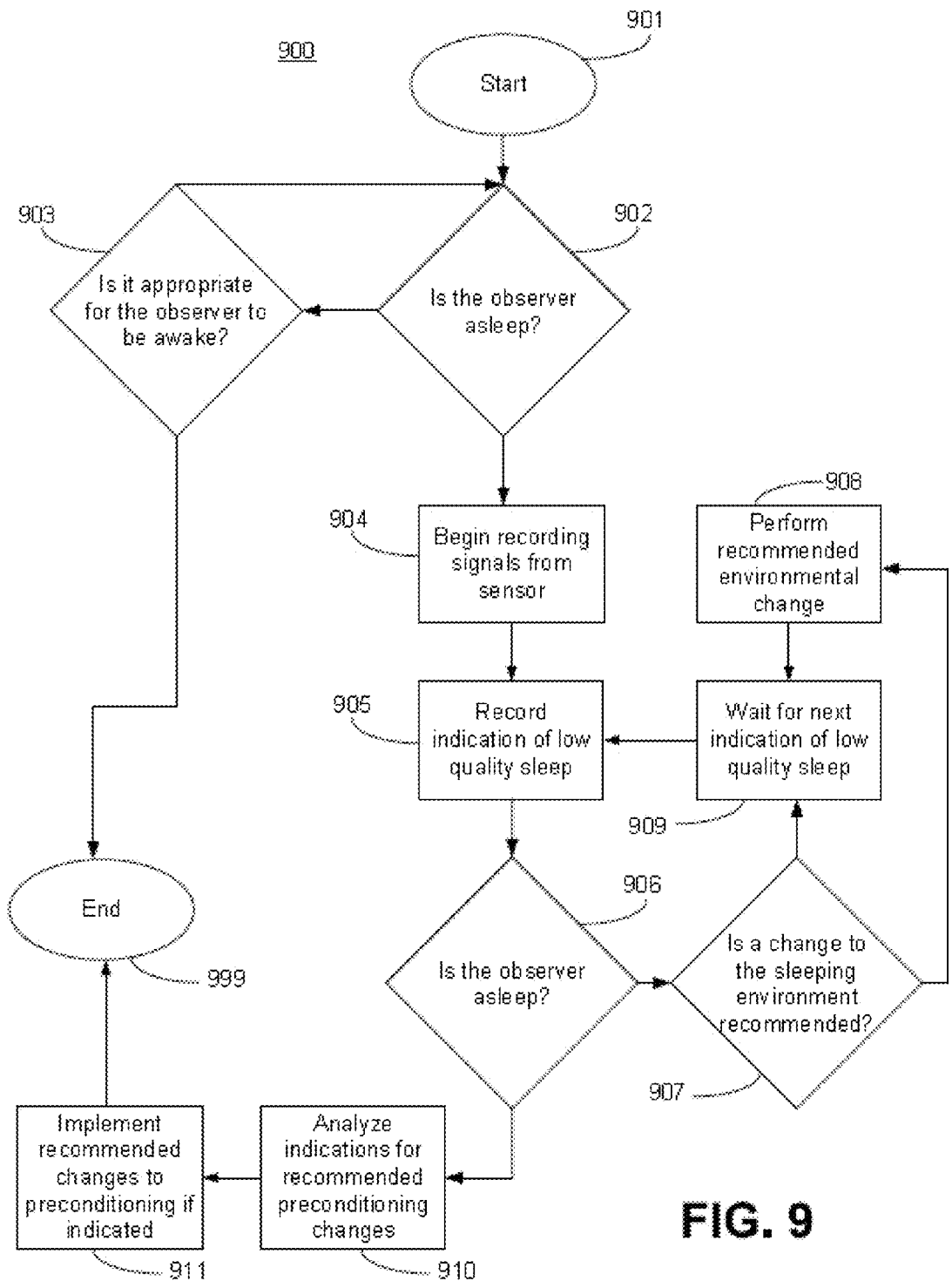
FIG. 9 is a flowchart illustrating a method for monitoring the quality of sleep of an individual and adjusting various environmental factors responsive thereto according to an embodiment of the invention.

Referring now to FIG. 9, a flow chart illustrating a method 900 for monitoring and improving the quality of sleep of an observer is presented. The method may be performed by a system for monitoring the quality of sleep and altering the environment within which the observer is sleeping responsive to indications of low quality sleep to improve the quality of sleep thereof. The system may be substantially similar to that of the system performing the method 800 of FIG. 8, further including one or more environmental control devices positioned in electrical communication with and being operable by the controller. Types of environmental control devices include, but are not limited to, HVAC systems, ceiling fans, floor fans, and noise generating devices.

Similar to method 800 of FIG. 8, method 900 may begin at Block 901, and then may determine if the observer is asleep at Block 902. If the observer is determined not to be asleep at Block 902, then at Block 903 the system may determine if the time of day indicates it is appropriate for the observer to be awake, as discussed hereinabove. If it is determined that it is appropriate for the observer to be awake, the method 900 may end at Block 999. If it is determined it is not appropriate for the observer to be awake, the method 900 may return to Block 902.

If, at Block 902, it is determined the observer is asleep, the system may begin recording signals sensor at Block 904. The signals from the sensor may indicate the quality of sleep of the observer. In that case of motion sensors, an indication of motion may be understood to mean lower quality sleep. Each indication of low quality sleep may be recorded by the system.

At Block 905, a signal indicating low quality sleep received by the system. At Block 906, the system may determine whether the observer is still asleep, similar to the determination made at Block 902. Upon recoding the signal, the method 900 may proceed to Block 907, wherein the system determines whether a change to the sleeping environment is recommended responsive to the indication of low quality sleep received at Block 905. Such a determination may be made based on a number of factors, including, the number of indications received within a timeframe, such as the previous five minutes. Such a timeframe is exemplary only, and any timeframe is contemplated and included within the scope of the invention.

Additionally, the determination may be made based on the potential for adverse sleeping conditions to be present, and the ability of the environmental control device to address such conditions. For example, where the environmental control device is an HVAC system, such systems typically include a thermometer that measures the temperature of air within a space and provides an indication thereof. Where the temperature is indicated to be outside a target temperature range for sleeping, the system may operate the HVAC system so as to bring the temperature to within the range. Where the environmental control system is a fan, the system may operate the fan, either increasing or decreasing the flow generated thereby, to accordingly alter the perceived temperature by the observer such that the perceived temperature falls within the target temperature range. In some embodiments, the environmental control system is a noise generating device, the system may alternatively increase or decrease the noise generated thereby, or, when possible, alter the type of noise generated, so as to encourage sleep in the observer. Such examples of environmental control devices are exemplary only, and any other type of environmental control device, as well as methods of operation, are contemplated and included within the scope of the invention.

If the determination is made at Block 907 to change the sleeping environment, the system may operate the environmental control device described hereinabove at Block 908. Then, at Block 909, the system may wait for the next signal indicating low quality sleep. When such a signal is received, the method 900 may return to Block 905.

If the determination is made at Block 907 not to change the sleeping environment, the method 900 may proceed to Block 909.

If, at Block 906, it is determine the observer is no longer asleep, the system may analyze the recorded indications of low quality asleep to determine if a change to the preconditioning schedule is recommended at Block 910, as described, hereinabove for FIG. 8. Additionally, any changes to the preconditioning schedule may be performed at Block 911, and the method 900 may end at Block 999.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention include all embodiments falling within the scope of the appended claims. Also, in the drawings and the description, there have been disclosed exemplary embodiments of the invention and although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A method of dynamically adjusting a circadian rhythm of an observer via a user device that includes control circuitry and an associated memory, the method comprising:
    accessing a calendar of the observer stored in the memory;
    identifying one or more future events of the observer to precondition for, defined as identified future events;
    determining a preconditioning schedule for at least one of the identified future events, including
        identifying a circadian shift needed, to the circadian rhythm of the observer, for the at least one identified future event,
        determining a magnitude of the circadian shift,
        determining a timeframe for preconditioning,
        determining a magnitude of a per-day shift based upon the timeframe, and
        determining if the per-day shift exceeds a maximum allowed per-day shift,
        upon a determination that the per-day shift exceeds the maximum allowed per-day shift, setting the preconditioning schedule responsive to the determination;
    establishing communication between the control circuitry and a light source; and
    operating the light source to emit light based upon the preconditioning schedule.

2. The method of claim 1 wherein identifying one or more future events includes determining a time zone within which the future event will occur.

3. The method of claim 1 wherein identifying one or more future events includes:
    accessing future events within a time period from the calendar; and
    determining which future events need preconditioning.

4. The method of claim 1 further comprising:
    determining if preconditioning schedules for the identified future events conflict;
    upon a determination that no conflict exists, operating the light source to emit light of the preconditioning schedules; and
    upon a determination that a conflict exists:
        querying a user to select one or more non-conflicting future events,
        receiving an input from the user indicating one or more future events to precondition for, and
        operating the light source responsive to the input.

5. The method of claim 1 wherein, upon a determination that the per-day shift exceeds the maximum allowed per-day shift, further performing:
    querying the user as to whether to override the maximum allowed per-day shift;

receiving an input from the user responsive to the query of whether to exceed the maximum per-day shift; and selecting the preconditioning schedule responsive to the user input.

6. The method of claim 5 wherein the maximum allowed per-day shift is 2.5 hours.

7. The method of claim 1 further comprising:

monitoring a sleep cycle of the observer; and implementing changes to the preconditioning schedule responsive to the sleep cycle of the observer.

8. The method of claim 7 wherein the step of monitoring a sleep pattern of the observer comprises:

determining if the observer is asleep:

recording signals from a sleep sensor;

identifying and recording an indication of low quality sleep from the signals received from the sleep sensor; and determining changes to the preconditioning schedule responsive to the indication of the low quality sleep.

9. The method of claim 8 wherein the sleep sensor is at least one of an optical motion detector and an acceleration detector.

10. A method of dynamically adjusting a circadian rhythm of an observer via a user device that includes control circuitry and an associated memory, the method comprising:

accessing a calendar of the observer stored in the memory;

identifying a future event of the observer to precondition for, defined as an identified future event;

determining a preconditioning schedule responsive to the identified future event, by identifying a circadian shift needed, to the circadian rhythm of the observer, for the identified future event, determining a magnitude of the circadian shift and a related magnitude of a per-day shift needed for the identified future event, and determining if the magnitude of the per-day shift exceeds a maximum allowed per-day shift, and selecting the preconditioning schedule based thereon;

establishing communication between the control circuitry and a light source; and operating the light source to emit light based upon the preconditioning schedule.

11. The method of claim 10 wherein identifying the future event includes determining a time zone within which the future event will occur.

12. The method of claim 10 wherein identifying the future event includes:

accessing future events within a time period from the calendar; and determining which future events need preconditioning.

13. The method of claim 10 wherein, upon a determination that the magnitude of the per-day shift exceeds the maximum allowed per-day shift, further performing:

querying the user as to whether to override the maximum allowed per-day shift;

receiving an input from the user responsive to the query of whether to exceed the maximum per-day shift; and selecting the preconditioning schedule responsive to the user input.

14. The method of claim 13 wherein the maximum allowed per-day shift is 2.5 hours.

15. A lighting system for dynamically adjusting a circadian rhythm of an observer, the system comprising:

a user device comprising control circuitry and associated memory; and a light source configured for communication with the control circuitry;

wherein the control circuitry is configured to access a calendar of the observer stored in the memory, identify one or more future events of the observer to precondition for, defined as identified future events, determine a preconditioning schedule responsive to the identified future event, by identifying a circadian shift needed, to the circadian rhythm of the observer, for the identified future event, determining a magnitude of the circadian shift and a related magnitude of a per-day shift needed for the identified future event, and determining if the magnitude of the per-day shift exceeds a maximum allowed per-day shift, and selecting the preconditioning schedule based thereon, establish communication with the light source, and control the light source to emit light based upon the preconditioning schedule.

16. The lighting system of claim 15 wherein the user device further comprises a communication device configured for communication with the control circuitry and configured to communicate across a network; and wherein the communication device is configured to access the calendar and identify future events associated with the observer via the network.

17. The lighting system of claim 15 wherein the control circuitry is further configured to determine a time zone within which the future events will occur.

18. The lighting system of claim 15 wherein the control circuitry is further configured to:

access future events within a time period from the calendar; and determine which future events need preconditioning.

19. The lighting system of claim 15 wherein, upon a determination that the per-day shift exceeds the maximum allowed per-day shift, the control circuitry is further configured to:

query the user as to whether to override the maximum allowed per-day shift;

receive an input from the user responsive to the query of whether to exceed the maximum per-day shift; and set the preconditioning schedule responsive to the user input.

20. The lighting system of claim 19 wherein the maximum allowed per-day shift is 2.5 hours.

21. The lighting system of claim 15 further comprising a sleep sensor configured to, in combination with the control circuitry, monitor a sleep cycle of the observer; wherein the control circuitry is further configured to implement changes to the preconditioning schedule responsive to the sleep cycle of the observer.

22. The lighting system of claim 21 wherein the sleep sensor comprises at least one of an optical motion detector and an acceleration detector.

* * * * *